(12) United States Patent
Shippert

(10) Patent No.: US 7,294,138 B2
(45) Date of Patent: Nov. 13, 2007

(54) NOSE PACK METHOD AND APPARATUS

(76) Inventor: Ronald D. Shippert, 4975 S. Albion St., Littleton, CO (US) 80121

( * ) Notice: Subject to any disclaimer, the term of this patent is extended or adjusted under 35 U.S.C. 154(b) by 164 days.

(21) Appl. No.: 10/879,385

(22) Filed: Jun. 28, 2004

(65) Prior Publication Data

US 2005/0288620 A1    Dec. 29, 2005

(51) Int. Cl.
| | |
|---|---|
| A61M 29/00 | (2006.01) |
| A61M 31/00 | (2006.01) |
| A61M 1/00 | (2006.01) |
| A61F 13/20 | (2006.01) |
| A61F 5/44 | (2006.01) |

(52) U.S. Cl. .................. 606/196; 604/11; 604/104; 604/286; 604/328; 604/540; 604/904; 604/913; 606/162; 606/199

(58) Field of Classification Search .................. 604/1, 604/11, 104, 285, 286, 540, 327, 328, 385.17, 604/904, 907, 913; 606/191, 196, 199, 162; 128/206.11
See application file for complete search history.

(56) References Cited

U.S. PATENT DOCUMENTS

| | | | | | |
|---|---|---|---|---|---|
| 592,659 | A | * | 10/1897 | Miller et al. | 604/286 |
| 1,042,624 | A | * | 10/1912 | Wagoner | 607/138 |
| 1,133,770 | A | * | 3/1915 | Wedler | 128/202.16 |
| 1,235,095 | A | * | 7/1917 | Beck | 606/196 |
| 1,561,020 | A | * | 11/1925 | Pond | 604/287 |
| 1,887,526 | A | * | 11/1932 | Spielberg et al. | 604/287 |
| 2,691,985 | A | * | 10/1954 | Newsom | 606/196 |
| 2,877,767 | A | * | 3/1959 | Kramer | 604/11 |
| 3,049,125 | A | * | 8/1962 | Kriwkowitsch | 606/196 |
| 3,570,494 | A | * | 3/1971 | Gottschalk | 606/196 |
| 3,690,321 | A | * | 9/1972 | Hirschman et al. | 604/359 |
| 3,696,703 | A | * | 10/1972 | Fox | 86/20.15 |
| 3,850,176 | A | * | 11/1974 | Gottschalk | 606/196 |
| 3,884,241 | A | * | 5/1975 | Walker | 606/199 |
| 3,905,372 | A | | 9/1975 | Denkinger | 128/285 |
| 3,938,517 | A | | 2/1976 | Anderson | 128/271 |
| 4,030,504 | A | | 6/1977 | Doyle | 128/325 |
| 4,213,452 | A | | 7/1980 | Shippert | 128/89 |
| 4,286,596 | A | * | 9/1981 | Rubinstein | 604/244 |
| 4,365,621 | A | * | 12/1982 | Brundin | 128/831 |
| 4,457,756 | A | | 7/1984 | Kern et al. | 604/286 |
| 4,563,182 | A | | 1/1986 | Stoy et al. | 604/285 |

(Continued)

FOREIGN PATENT DOCUMENTS

EP    0 354 704 A1 *  2/1990

OTHER PUBLICATIONS www.shippertmedical.com.*

Primary Examiner—Tatyana Zalukaeva
Assistant Examiner—Michael G Bogart
(74) Attorney, Agent, or Firm—Sheridan Ross P.C.

(57) ABSTRACT

A medical device and method for treating nose bleeds are provided. The device includes packing material interconnected to a flange member. The packing material is insertable into a nasal cavity, for absorbing blood and other body fluids. The flange member prevents the packing material from being inhaled or otherwise moving in an anterior direction. In addition, the flange member obscures a view of the interior of the user's nasal cavity, and therefore of blood within the cavity, or of blood that has been absorbed by the packing member.

31 Claims, 6 Drawing Sheets

U.S. PATENT DOCUMENTS

| | | | |
|---|---|---|---|
| 4,568,326 A | | 2/1986 | Rangaswamy ............... 604/1 |
| 4,646,739 A | | 3/1987 | Doyle ...................... 128/325 |
| 4,895,559 A | * | 1/1990 | Shippert .................... 604/15 |
| 5,011,474 A | * | 4/1991 | Brennan ................... 604/540 |
| 5,327,897 A | * | 7/1994 | Andresen .................. 600/575 |
| 5,374,261 A | * | 12/1994 | Yoon ..................... 604/385.01 |
| 5,383,891 A | | 1/1995 | Walker ..................... 606/196 |
| 5,568,808 A | * | 10/1996 | Rimkus ................ 128/206.11 |
| 5,584,822 A | | 12/1996 | Lively et al. ............... 604/286 |
| 5,713,855 A | * | 2/1998 | Shippert ................... 604/516 |
| 5,788,663 A | | 8/1998 | Igaue et al. ................. 604/15 |
| 5,827,224 A | | 10/1998 | Shippert .................... 604/73 |
| 5,890,491 A | * | 4/1999 | Rimkus ................ 128/206.11 |
| 5,895,408 A | * | 4/1999 | Pagan ...................... 606/199 |
| 5,919,170 A | * | 7/1999 | Woessner .................. 604/264 |
| 6,039,716 A | * | 3/2000 | Jessup et al. ......... 604/385.18 |
| 6,123,697 A | | 9/2000 | Shippert .................... 604/514 |
| 6,129,175 A | * | 10/2000 | Tutor et al. ................. 181/135 |
| 6,183,436 B1 | * | 2/2001 | Korteweg et al. ....... 604/96.01 |
| 6,216,694 B1 | | 4/2001 | Chen ..................... 128/206.11 |
| 6,464,670 B1 | * | 10/2002 | Mulholland ................. 604/288 |
| 6,517,509 B1 | * | 2/2003 | Shippert .................... 604/11 |
| 6,536,437 B1 | | 3/2003 | Dragisic ................ 128/207.18 |
| 6,890,324 B1 | * | 5/2005 | Jackson et al. ........ 604/385.17 |
| 6,971,387 B2 | * | 12/2005 | Michaels ............... 128/206.11 |
| 2003/0167048 A1 | | 9/2003 | Policappelli .......... 604/385.17 |
| 2006/0036206 A1 | * | 2/2006 | Yokoyama et al. ............ 604/1 |

* cited by examiner

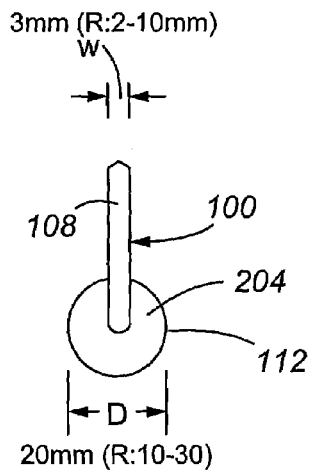
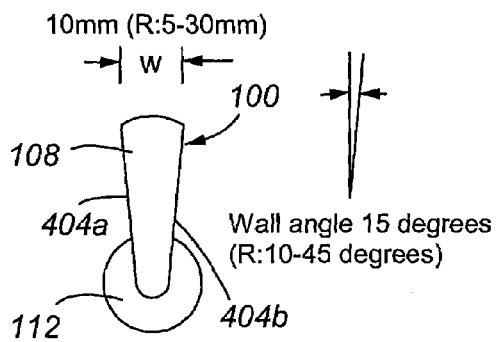
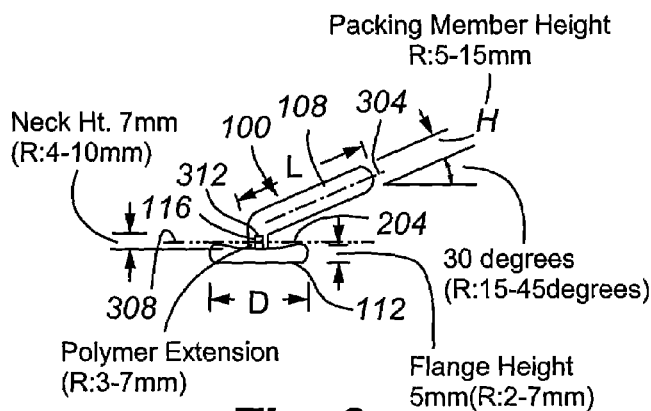
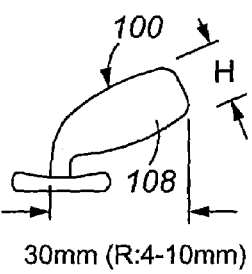
Fig. 2
Fig. 4
Fig. 3
Fig. 5

NOSE PACK METHOD AND APPARATUS

FIELD OF THE INVENTION

The present invention relates to the treatment of nosebleeds. In particular, the present invention allows fluid associated with nosebleeds to be absorbed, while blocking a view of such fluids.

BACKGROUND OF THE INVENTION

As a result of bodily injuries or certain medical conditions, it is oftentimes necessary to utilize a nasal pack to treat nosebleeds. Such a need can arise during sporting events, in emergency situations and in surgery. In general, existing devices include an absorbent packing material with an extension of some kind that remains outside of the nasal cavity to position and/or secure the absorbent material.

Of special importance is the "show" of blood during a sporting or a social event. It is no longer acceptable for blood to show because people are fearful that the blood may be contaminated, for example with Hepatitis or HIV. In fact, in connection with organized sporting events, a player can often continue playing if no blood is seen by the referee. In other words, the player can continue play if the active bleed is "contained" in a pack and there is no visible blood. In the case of emergency or surgical use, containment of blood with a pack is also desirable, as uncontainment can lead to costly cleanup measures as well as exposure of medical personnel to possible infectious fluids.

When conventional packs are in the nose, the anterior end of the pack can be seen through the opening of the nose. Accordingly, blood is visible and sometimes actually drips out the porous surface of the pack. Accordingly, the blood is not completely contained and can be an unnecessary hazard. Also, conventional packs often use strings that are looped around the ear to prevent aspiration of the pack. However, during sporting events these strings can catch on surrounding items. In addition, the stability of conventional packs is a constant problem. In particular, when packs soak up blood they become heavier and slick. Gravity tends to pull the pack in an anterior direction, which can result in the pack falling out of the nasal cavity. Normal inspiration tends to pull the pack in a posterior direction, with the possibility of swallowing or aspirating the pack, which can be life endangering.

SUMMARY OF THE INVENTION

In accordance with embodiments of the present invention, a nasal pack having an absorbent section or packing member that is molded to a flange member is provided. The flange member may be formed from an opaque material, and may be shaped to substantially cover the nasal cavity opening or nostril. In addition to blocking a view of blood that is absorbed by the packing member, the flange member prevents movement of the packing member in a posterior direction, and allows the nasal pack to be removed easily for changing or after it is no longer needed.

In accordance with embodiments of the present invention, the flange member comprises a non-absorbent section having a surface that is substantially planar to, and at least slightly larger than, the nostril. In addition, an extension or protrusion extends from the surface, to which the packing member is interconnected. In addition to providing a structure for molding or otherwise attaching the packing member to the flange member, certain embodiments with such an extension can cause a neck portion to be formed in the end of the packing member that is non-absorbent or substantially non-absorbent, such that the portion of the device that is likely to become visibly bloody is positioned posterior with respect to the opening to the nasal cavity. In addition, a neck portion that is non-absorbent or substantially non-absorbent can facilitate removal of the nasal pack by avoiding adhesion between the nasal pack and the nasal cavity at the anterior end of the packing member.

In accordance with embodiments of the present invention, the body of the packing member is absorbent and expands as it soaks up blood and/or other fluids. Such expansion can exert pressure on the walls of the nasal cavity to control bleeding, and contributes to the secure positioning of the device with respect to the nasal cavity. To provide additional resistance to anterior movement, the packing member may be tapered such that the width of the member at the posterior end is greater than the width of the member at the anterior end, thereby forming a wedged configuration. Alternatively or in addition, swelling or expansion of the packing member at the anterior end may be restricted or prevented as a result of the absorbent member being molded to the flange member.

In accordance with still other embodiments of the present invention, the packing member is molded to the flange member such that the length of the packing member is at an angle to the surface of the flange member. This angle may be up to and including 90°. Furthermore, such embodiments may include a packing member having a neck portion interconnecting the length of the absorbent member that is at an angle to the surface of the flange member to the flange member. If provided, the neck portion may coincide with the portion of the absorbent member that is molded to the flange member at the flange member extension.

In accordance with further embodiments of the present invention, two separate packing members may be interconnected to a single flange member. According to such embodiments, the two packing members are separated from one another by a distance that allows the assembly to be inserted into both nostrils of a user at the same time. According to such embodiments, the flange member has a width that allows it to extend across, and block the view of, the interior passageways of both nasal cavities.

In accordance with still other embodiments of the present invention, a method for treating nosebleeds and preventing a view of blood is provided. According to such a method, a packing member is inserted into an existing naval cavity. The packing member absorbs fluids, and furthermore expands when fluids have been absorbed. The packing member is inserted into the nostril until a flange member contacts or is placed in close proximity to the opening to the nasal cavity. Once in such a position, the packing member is able to absorb blood or other body fluid, expanding the packing member, and thereby preventing the packing member from moving in an anterior direction. In addition to preventing anterior movement, the expansion of the packing member applies pressure to one or more walls within the nasal cavity. Furthermore, the flange member is sized to prevent the packing member from moving in a posterior direction. In addition, the flange member may be sized so that it substantially covers the opening to the nasal cavity, preventing onlookers from a view of the interior of the nasal cavity while the packing material and attached flange are in position.

According to further embodiments of the present invention, placement of the packing member within the nasal cavity includes inserting the packing member in an anterior portion of the nasal cavity, and turning the assembly to allow the packing member to extend into the posterior portion of the nasal cavity as the assembly is further inserted. Final positioning of the assembly may therefore include inserting it until the packing member is substantially parallel to the floor of the nasal cavity, and the flange member is at a small angle to the floor of the nasal cavity, and such that it is substantially parallel to a plane defined by the nasal opening.

In accordance with embodiments of the present invention, a prepackaged nosebleed kit is provided. The kit includes a packing device, disposable gloves, a disposable emesis basin, disposable gauze pads, tape, coagulant, a scoop for pickup of the coagulant, medical waste type baggie for disposal, a disinfectant packet to clean contaminated areas, a handy clean packet for cleaning up the patient, and instructions.

Additional advantages of the present invention will become more readily apparent from the following discussion, particularly when taken together with the accompanying drawings.

BRIEF DESCRIPTION OF THE DRAWINGS

FIG. 2 is a top plan view of a medical device in accordance with embodiments of the present invention, in a compressed state;

FIG. 3 is a lateral view of a medical device in accordance with embodiments of the present invention, in a compressed state;

FIG. 4 is a top plan view of a medical device in accordance with embodiments of the present invention, in an expanded state;

FIG. 5 is a lateral view of a medical device in accordance with embodiments of the present invention, in an expanded state;

DETAILED DESCRIPTION

Figure 1:
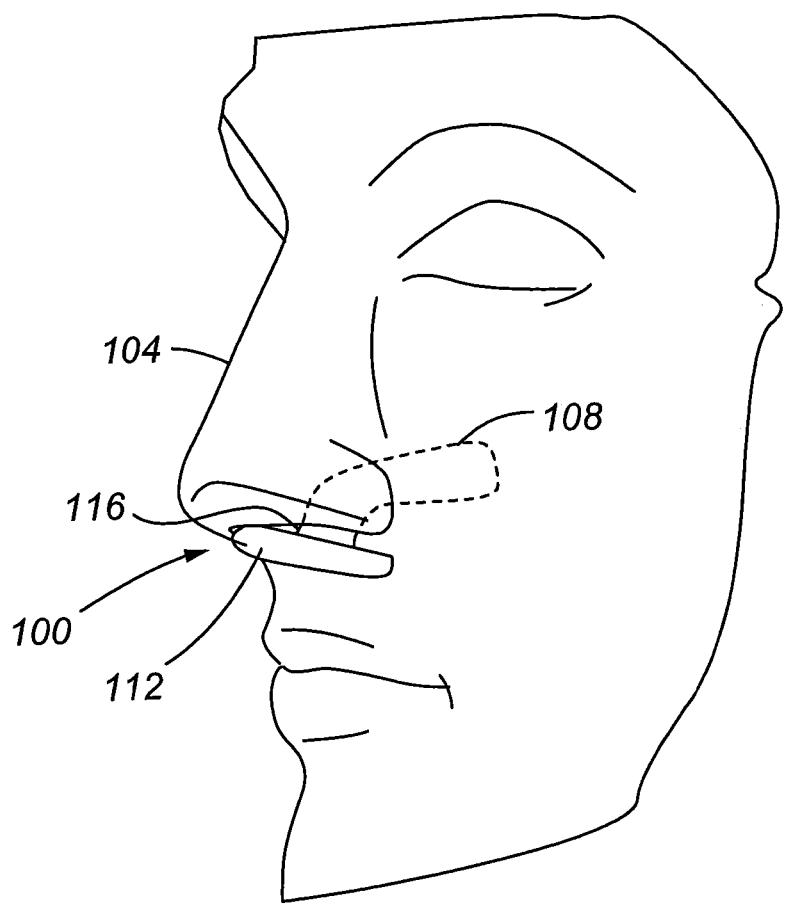
FIG. 1 illustrates a medical device in accordance with embodiments of the present invention inserted within the nasal cavity of a user.

With reference now to FIG. 1, a medical device 100 in accordance with embodiments of the present invention, inserted in a nasal cavity of a user 104, is illustrated. In general, the medical device 100 includes a packing member 108 that absorbs blood and other body fluids, interconnected to a flange member 112 at an extension 116 of the flange member. The flange member 112 serves to prevent movement of the device 100 in a posterior direction. The flange 112 is sized so that, when positioned as illustrated in FIG. 1, a view into the nasal cavity of the user 104 is obscured. In addition, the flange member 112 assists in the placement and removal of the medical device 100.

With reference now to FIG. 2, a top plan view of a medical device 100 in accordance with embodiments of the present invention is illustrated in a compressed state. In particular, the packing member 108 may be compressed prior to initial use, to assist in the placement of the device 100 within the nasal cavity of the user 104. In accordance with embodiments of the present invention, the width W of the packing member 108 may be from about 2 mm to about 10 mm. In accordance with still other embodiments of the present invention, the width W of the packing member 108 may be about 3 mm. As used herein, and as can be appreciated by one of skill in the art, a dimension may be considered to be within "about" a stated dimension if the measured length is within 1.0 mm of the stated length. The flange member 112 interconnected to the packing member 108 has at least a first dimension that is sufficient to prevent the device 100 from moving in a posterior direction when it is inserted in the nasal cavity of a user 104. Furthermore, as illustrated in FIG. 2, the flange member 112 may include a surface 204 that is shaped and sized so as to prevent a view of the interior of the nasal cavity when the device 100 is in place. The flange member 112 may provide an extension or protrusion 116 to facilitate interconnection of the packing member 108 to the flange member 112. In accordance with embodiments of the present invention, the diameter D of the flange member 112 may be from about 10 mm to about 30 mm. In accordance with still other embodiments, the diameter D of the flange member 112 may be about 10 mm.

With reference now to FIG. 3, a medical device 100 in accordance with embodiments of the present invention is shown in a lateral view, with the packing member 108 in a compressed state. As seen in FIG. 3, the packing member 108 may be interconnected to the flange member 112 such that the longitudinal axis 304 of the packing member 108 is at an angle with respect to a plane 308 defined by the surface 204 of the flange member 112 that is proximate to the nostril of the user 104 when the device 100 is positioned within the user's nasal cavity. A neck portion 312 is formed in the packing member 108 where the packing member 108 is interconnected to the extension 116 of the flange member 112.

The length L of the packing member 108 may be from about 10 mm to about 100 mm. In accordance with further embodiments, the length of the packing member 108 may be about 40 mm. The height H of the packing member 108 may be from about 5 mm to about 15 mm. In accordance with embodiments of the present invention, the height H of the packing member 108 is about 7 mm.

The thickness T of the flange member 112, at outer portions of the flange member 112 may be from about 2 mm to about 7 mm. In accordance with other embodiments, the thickness at the edges of the flange member 112 may be about 5 mm. In accordance with still further embodiments, the thickness of the flange member 112 may be thinner at medial portions of the flange member 112, for example in an area proximate to the extension 116, than at the edges. The surface 204 of the flange member 112 may be planar, or it may be contoured, for example to follow the contour of the nose of a user 104. In accordance with embodiments of the present invention, the extension 116 extends from about 4 mm to about 10 mm from the surface 204 of the flange member 112. In accordance with other embodiments of the present invention, the extension 116 extends about 7 mm from the surface 204 of the flange member 112.

The angle of the longitudinal axis 304 of the packing member 108 with respect to the plane 308 defined by the flange member 112 may be from about 15° to about 45°. In accordance with further embodiments of the present invention, the angle between the longitudinal axis 304 of the packing member 108 and the plane 308 defined by the flange member 112 may be about 30°.

In accordance with embodiments of the present invention, the packing member 108 is formed from a material that absorbs fluids, including body fluids, such as blood. In certain embodiments, the packing member 108 is made from a polyvinyl alcohol (PVA) or polyurethane foam or sponge, or other foam materials, that is formed or manufactured into desired sizes. Furthermore, as the packing member 108 receives fluid, it expands to about 1.5 to 7 times its compressed or unexpanded state. As can be understood, the portions of the packing member 108 that expand are dependent upon their location in the nasal cavity. In particular, the expansion of the packing member 108 may be limited with respect to those portions of the packing member 108 that are in contact with the walls of the nasal cavity.

The flange member 112 may be formed from various materials that are substantially non-absorbent. The flange member 112 may also be formed from materials that resist bending or that are rigid. Alternatively, the flange member 112 may be at least partially flexible or padded, to provide a more comfortable fit. Examples of such materials include silicone, monprene, or other polymers. In addition, the flange member 112 may be formed from material that is less absorbent than the packing material 108. Examples of such materials include paper, cardboard or fiberboard. In accordance with further embodiments of the present invention, the flange member 112 is opaque. The flange member 112 may also be colored. The color of the flange member 112 may be a flesh color, to blend with the face of the user 104. Alternatively or in addition, the flange member 112 may be colored so that a view of blood absorbed by the packing member 108 is concealed. As another example, the flange member 112 and/or extension 116 can be formed from polyvinyl alcohol (PVA) that has been compressed so that it cannot expand. Additionally or alternatively, the packing member 108 can be formed from the same piece of PVA as the flange member 112, but is not so compressed that it cannot expand as it receives fluid.

In accordance with embodiments of the present invention, the packing member 108 is interconnected to the flange member 112 by molding the two components 108, 112 together. More particularly, the neck portion 312 of the packing member 108 may be molded or fused to the extension 116 provided by the flange member 112. In accordance with other embodiments, the packing member 108 may be interconnected to the flange member 112 by riveting, stitching, heat sealing, adhering, or chemical bonding. In accordance with still other embodiments of the present invention, the method of interconnecting the packing member 108 to the flange member 112 is selected so that the packing member 108 is made substantially non-absorbent in the neck portion 312, such that blood or other fluids absorbed by the packing member 108 in general are not absorbed, and therefore are not visible, at the neck portion 312. Furthermore, in embodiments providing a non-absorbent neck portion 312, the absorbent body portion is positioned further up the nasal cavity, thereby making the bloody portion of the device 100 more difficult to see.

With reference now to FIG. 4, a top view of a medical device 100 in accordance with embodiments of the present invention is illustrated, with the packing member 108 in a fully expanded state. In such a state, the width of the packing member 108 at an anterior portion, proximate the flange member 112, is less than the width W at the posterior portion. In accordance with embodiments of the present invention, the difference in widths creates a substantially wedge shaped profile. Furthermore, the difference in angle between opposite sidewalls 404a and 404b of the packing member 108 may be from about 10° to about 45°. In accordance with still other embodiments of the present invention, the angle between opposite sidewalls 404a, 404b may be about 15°. As used herein, a measured angular dimension is "about" equal to a stated angular dimension if the measured dimension is within 1.0° of the stated dimension. In accordance with embodiments of the present invention, the width W of the packing member 108 in an expanded condition at a posterior portion may range from about 5 mm to about 30 mm. In accordance with further embodiments of the present invention, the width W of the posterior portion of the packing member 108 may be about 10 mm when in an expanded condition.

With reference now to FIG. 5, a medical device 100 in accordance with embodiments of the present invention in an expanded condition is shown in a lateral view. In such an expanded condition, the length L of the packing member 108 may remain at or about the unexpanded length, namely from about 10 mm to about 100 mm, while the height H of the packing member 108 may have expanded to from about 10 mm to about 40 mm. In accordance with other embodiments of the present invention, the height H of the packing member 108 in an expanded condition may be about 30 mm.

As can be appreciated by one of skill in the art from the description provided herein, the packing member 108 will typically not achieve a fully expanded condition such as illustrated in FIGS. 4 and 5 when in use. In particular, when inserted in a nasal cavity of a user 104, the expansion of the packing member 108 will typically be constrained by the distance between the various walls of the nasal cavity. However, as can also be appreciated by one of skill in the art from the description provided herein, embodiments of the present invention that provide a packing member 108 capable of expansion beyond the dimensions of the nasal cavity in which the medical device 100 is inserted facilitate the application of pressure to the walls of the nasal cavity.

Figure 6:
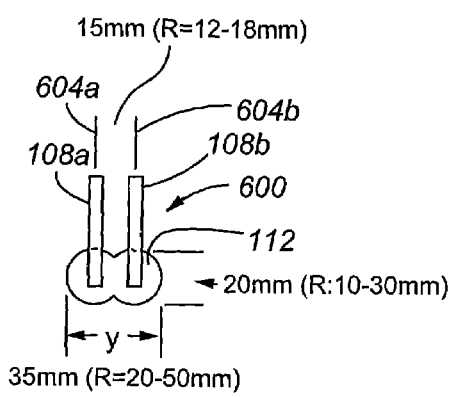
FIG. 6 is a top plan view of a medical device in accordance with other embodiments of the present invention, in a compressed state.
Figure 7:
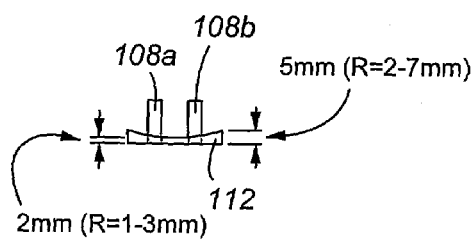
FIG. 7 is a front view of a medical device in accordance with other embodiments of the present invention, in a compressed state.

With reference now to FIGS. 6 and 7, a medical device 600 in accordance with further embodiments of the present invention is illustrated. In general, an embodiment as illustrated in FIGS. 6 and 7 includes first 108a and second 108b packing members interconnected to a common flange member 112. As shown, the packing members 108a, 108b may be substantially parallel to one another, such that they may each be inserted into both nasal cavities of a user 104. Accordingly, each packing member 108a, 108b of a medical device 600 may be dimensioned like a packing member 108 included in an embodiment for use in a single nostril (e.g., a medical device 100 as illustrated in FIGS. 1-5). In addition, a centerline 604a of the first packing member 108a may be separated from a centerline 604b of the second packing member 108b by distance of from about 12 mm to about 18 mm. In accordance with further embodiments of the present invention, the distance between the centerlines 604a, 604b of the packing members 108a, 108b may be about 15 mm.

The flange member 112 provided in connection with a medical device 600 for use in both nostrils simultaneously may be sized so as to cover or obscure the view of both nostrils of a user when the device 600 is inserted into the nasal cavities of the user 104. Accordingly, the flange member 112 may have a lateral dimension y of from about 20 mm to about 50 mm. In accordance with further embodiments of the present invention, the flange member 112 may have a lateral dimension y of about 35 mm.

Figure 8:
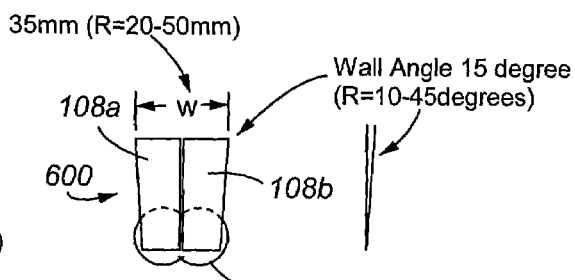
FIG. 8 is a top plan view of a medical device in accordance with other embodiments of the present invention, in an expanded state.
Figure 9:
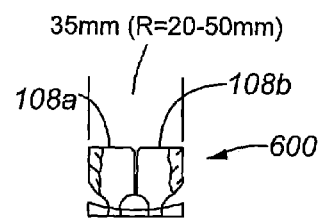
FIG. 9 is a front view of a medical device in accordance with other embodiments of the present invention, in an expanded state.

With reference now to FIGS. 8 and 9, a medical device 600 providing a packing member 108 for each nasal chamber of a user is illustrated, with the packing members 108a, 108b shown in their expanded form. As noted above, a medical device 600 having two packing members 108a, 108b may have each of those packing members 108a, 108b sized like a single packing member 108 according to single nasal chamber embodiments. The width across both packing members 108a, 108b may be from about 20 mm to about 50 mm. In accordance with additional embodiments of the present invention, the width of the packing members 108a, 108b taken together may be about 35 mm when the packing members 108 are in an expanded form. This dimension may be less than twice the expanded dimension of a single packing member 108, due to interference between the adjacent packing members 108a, 108b in dual nasal chamber embodiments.

Figure 10:
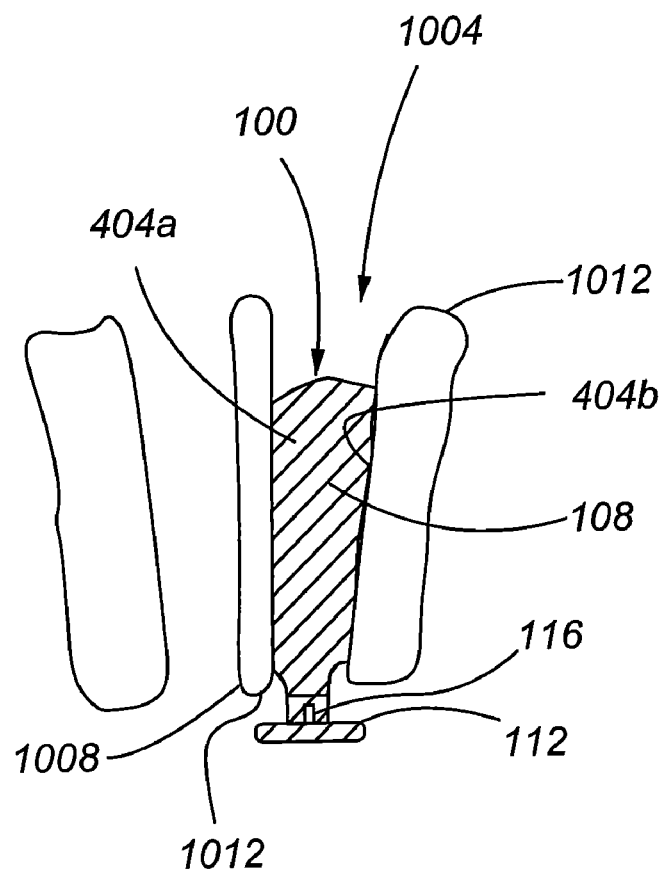
FIG. 10 illustrates a medical device in accordance with embodiments of the present invention in use in a nasal passage.

With reference now to FIG. 10, a medical device 100 in accordance with embodiments of the present invention is shown positioned within a nasal cavity 1004 of a user. In particular, the packing member 108 of the medical device 100 is shown in an expanded form, with one of the lateral walls 404a pressed against a wall of the septum 1008, and the other of the lateral walls pressed against the turbinate 1012. Accordingly, it can be seen that the packing member 108 substantially fills the area between the walls of the nasal chamber 1004, in at least a portion of the nasal chamber 1004, to block a flow of blood or other body fluids from the nasal chamber 1004. In addition, this feature allows the packing member 108 to apply pressure to the walls of the nasal chamber 1004, to help stop the flow of blood and to inhibit movement of the device 100, particularly in an anterior direction. The flange member 112 remains outside of the nasal chamber 1004. As shown in FIG. 10, the flange member 112 is sized so that it covers all or substantially all (i.e., most) of the opening 1008 to the nasal chamber, preventing an onlooker from seeing blood that may have been absorbed by the packing member 108 inside the nasal chamber 1004. In addition, the neck portion 116 positions the expanded portion of the packing member 108 (i.e., the portion that contains blood or other fluid) back, away from the opening 1012 to the nasal chamber 1004, thus further obscuring a view of blood that may have been absorbed by the packing member 108.

Figure 11:
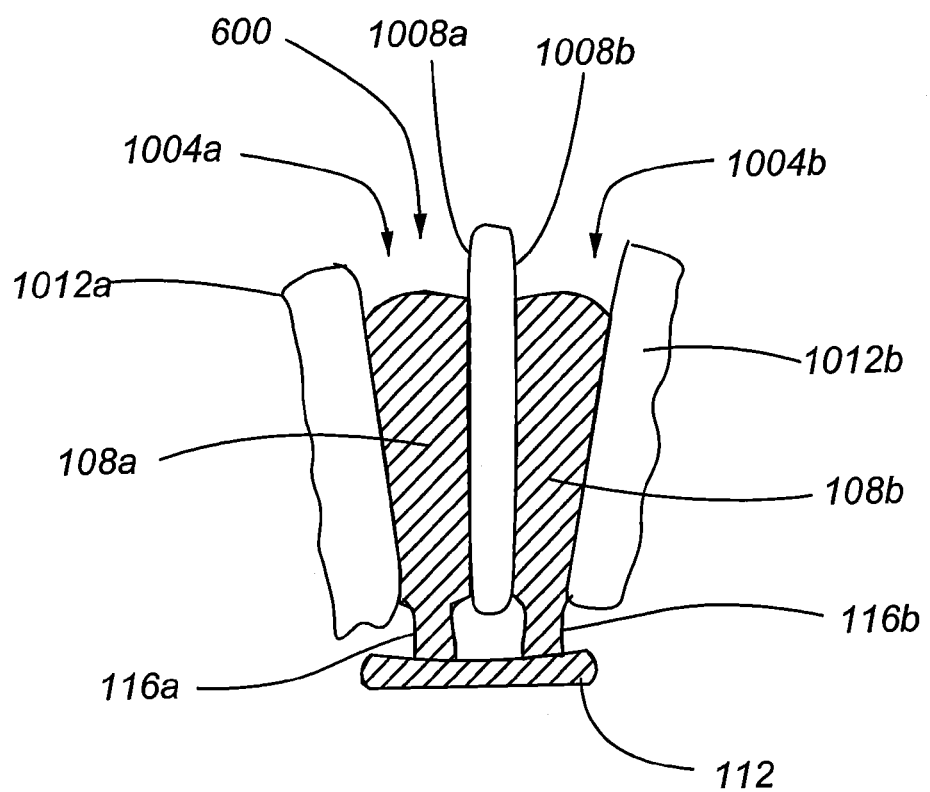
FIG. 11 illustrates a medical device in accordance with other embodiments of the present invention in use in nasal passages.

With reference now to FIG. 11, a cutaway view of a user's nasal chambers 1004a and 1004b, with a dual packing member medical device 600 in accordance with embodiments of the present invention inserted, is illustrated. In particular, it can be seen that each packing member 108a and 108b covers all or substantially all of the width of the nasal chamber 1004a or 1004b in which it is inserted, in at least a portion of the respective nasal chamber 1004, when it is in an expanded state. Accordingly, a user who is bleeding from both nostrils may use a double packing member device 600 to contain and obscure a view of blood flows from both nostrils.

By expanding against the walls 1012a and 1012b of the turbinates, and against the walls 1008a and 1008b of the septum, the packing members 108a and 108b of the medical device 600 can apply pressure to the walls of the nasal chambers 1004a, 1004b. In addition, movement of the medical device 600 is inhibited. Furthermore, in accordance with embodiments providing packing members 108a and 108b having a wedge shape, movement is particularly inhibited in an anterior direction. The flange member 116 generally lies outside of both nasal chambers 1004a and 1004b. In addition, the flange member 112 is sized such that it covers or obscures the openings to each of the nasal passages 1004a and 1004b, thereby preventing or obscuring a view of blood within the nasal chambers 1004a, 1004b, including blood that has been absorbed by the packing members 108a, 108b. In addition, the neck portions 116a and 116b can be seen to position the absorbent sections of the packing members 108 (i.e., the expanded portions) back from the opening of each of the nasal chambers 1004a, 1004b, further reducing the chance that an onlooker will see blood that has been absorbed by the packing members 108a, 108b.

Figure 12B:
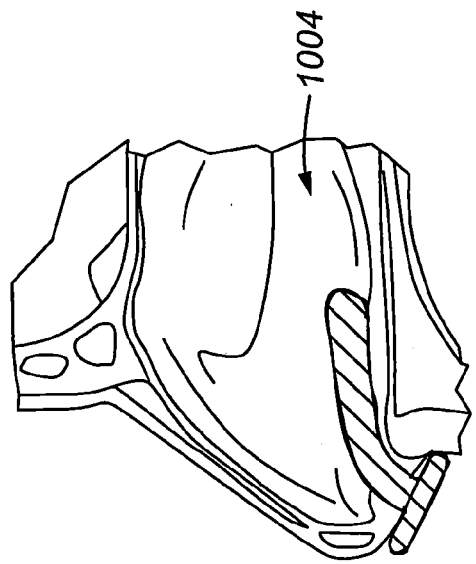
FIG. 12B illustrates a medical device in accordance with embodiments of the present invention inserted within a nasal cavity.
Figure 12A:
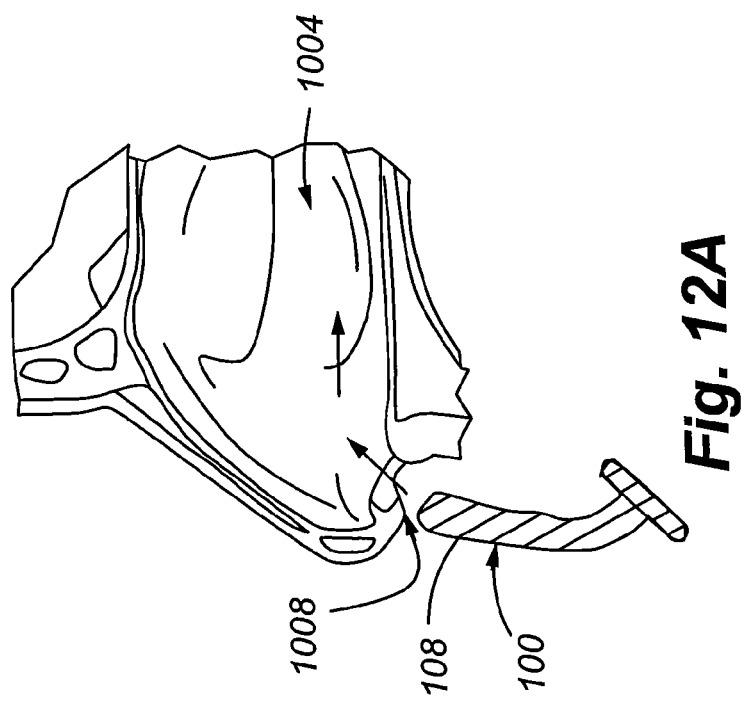
FIG. 12A illustrates the positioning of a medical device in accordance with embodiments of the present invention with respect to a nasal cavity, prior to insertion of the medical device in a nasal cavity.

With reference now to FIGS. 12A and 12B a nasal chamber 1004 of a user is shown in cross-section. In particular, a medical device 100 is shown being inserted into the nasal chamber 1004 of a user. As shown in FIGS. 12A and 12B, as a packing member 108 is inserted in a nostril or opening 1012 to a nasal chamber 1004, it will typically have a first orientation, as shown in FIG. 12A. When the packing member 108 is fully inserted in the nasal chamber 1004, it will have a second orientation (shown in FIG. 12B), that is between 45° and 90° from the orientation of the packing member 108 when it is initially inserted. In order to facilitate placement of the device 100, the packing member 108 of embodiments of the present invention has a longitudinal axis 304 that is positioned at an angle of between 15° and 45° with respect to a plane 308 defined by the surface of the flange member, as described elsewhere herein. In addition, as also described elsewhere, the neck portion 116 facilitates positioning of the device 100, such that the packing member 108 can rest on the floor of the nasal chamber 1004, without placing the flange 112 such that it places pressure on the user's nose.

The insertion of a double packing member 108 device 600 can be performed in essentially the same way as illustrated and described in connection with a medical device 100 having a single packing member 108. As can be appreciated from the description provided herein, in the case of a double packing member 108 device 600, the packing member 108 would be inserted in each nostril 1004 of the user simultaneously.

In accordance with further embodiments of the present invention, a method for treating nose bleeds is provided. The method may be performed using the components of a kit in accordance with embodiments of the present invention. In particular, a kit in accordance with embodiments of the present invention may include the following: an absorbent packing material; disposable polymer gloves for the operator; a disposable polymer emesis basin; disposable gauze pads; tape; blood coagulant; scoop for picking up coagulant; a medical waste disposal baggie; a disinfectant packet to clean contaminated areas; a handy clean packet for cleaning up the patient; and instructions. A sterile packet of lubricant and/or anesthetic may also be provided. In addition, the kit may include a nasal speculum, and/or forceps. The absorbent packing material or nasal pack provided as part of the kit may comprise a medical device 100 or 600 in accordance with embodiments of the present invention. Alternatively or in addition, other absorbent packs may be provided. In an exemplary embodiment, the gauze pads are sterile 4×4's, and the tape is a cloth or paper tape for securing gauze pads to a patient. The instructions may generally set forth use of the kit, for example as set forth in the method described herein.

In particular, a method in accordance with the present invention may proceed by placing the patient in an upright position, with embodiments of the head leaning forward. An emesis basis included in the kit is placed under the patient's chin to catch the dripping of blood from mouth and the nose. The operator puts on sterile gloves from the kit. In connection with a nose bleed, blood has usually appeared in the mouth via the nasopharynx pathway and the patient is instructed to spit blood appearing in his mouth into the emesis basin. Gauze pads from the kit are placed over the nose, and the patient is instructed to squeeze the nares firmly without relief while operator gets the nasal pack reader. The nasal pack may comprise a medical device 100, 600 as described elsewhere herein, or another pack. The pack is taken out of its sterile packet, and a lubricant and/or anesthetic is expressed from provided tubes onto the tip of the packing device. The patient is instructed to remove the gauze pad, and the operator uses a nasal speculum included in the kit to widen the opening or openings to the nasal cavity or cavities for visibility and easy entrance of the packing material. The packing material is then inserted into the nasal cavity and pushed inward in a plane horizontal to the floor of the nasal cavity or cavities. A clean gauze pad is then placed on the nares and the patient is instructed to keep pressure on the nares until the bleeding stops. Clean up then begins. The face is cleaned with a handy wipe included in the kit. Any blood on the floor may have coagulant included in the kit sprinkled on it to produce a coagulum. A provided scoop is then used to place the coagulant into the special medical disposal bag. All bloody gauze pads, the used gloves, the used packaging, the speculum, and any forceps used to assist in placing packing material are then placed in the same disposal bag, ready for medical disposal. The blood will have now been contained.

As can be appreciated from the description provided herein, where a kit as described above includes a medical device 100, 600 as described herein, the blood will be obscured from view, as well as contained. Accordingly, for example when used in sporting or other social situations during which the appearance of blood is discouraged, blood may be effectively contained and/or concealed.

The foregoing discussion of the invention has been presented for purposes of illustration and description. Further, the description is not intended to limit the invention to the form disclosed herein. Consequently, variations and modifications commensurate with the above teachings, within the skill and knowledge of the relevant art, are within the scope of the present invention. The embodiments described herein above are further intended to explain the best mode presently known of practicing the invention and to enable others skilled in the art to utilize the invention in such or in other embodiments and with various modifications required by their particular application or use of the invention. It is intended that the appended claims be construed to include alternative embodiments to the extent permitted by the prior art.

What is claimed is:

1. A device for applying pressure and absorbing liquid in a nasal cavity, comprising:
    a flange member, wherein said flange member includes an integral extension, and wherein said integral extension is substantially rigid and non-absorbent; and
    an absorbent packing member formed from a unitary piece of material, having:
        a length;
        a pair of planar sidewalls, wherein said sidewalls have equal areas;
        a posterior portion including a free end of said packing member; and
        an anterior portion, said anterior portion including a non-absorbent neck portion,
    wherein said integral extension extends from a surface of said flange member facing said packing member, and wherein said surface of said flange facing said packing member defines a plane,
    wherein in an expanded condition a width of said posterior portion increases in a direction away from said anterior portion in a region beginning at a section including said integral extension of said flange member and said neck portion and extending to an end of the sidewalls proximate to the free end of the packing member,
    wherein said integral extension of said flange member is fixed to said packing member at said neck portion of said anterior portion, and
    wherein said sidewalls are substantially symmetrical with respect to said plane defined by said flange, and wherein said absorbent packing member is not enclosed within a cover.

2. The device of claim 1, wherein said flange member is non-absorbent.

3. The device of claim 2, wherein said flange member includes:
    a substantially planar surface, wherein said extension portion of said flange member is fused to said neck portion of said packing member.

4. The device of claim 3, wherein said substantially planar surface has at least a first dimension, wherein said first dimension is at least twice the width of said anterior portion of said packing member.

5. The device of claim 4, wherein said extension protrudes from said at least a first surface.

6. The device of claim 4, wherein at least most of said length of said packing member is at an angle to said substantially planar surface.

7. The device of claim 1, wherein said flange member is opaque.

8. The device of claim 1, wherein said flange member is formed from a polymer material, and wherein said polymer material is at least partially absorbed by said packing member at said neck portion, whereby said neck portion of said packing member is non-absorbent.

9. The device of claim 1, further comprising first and second packing members, wherein said flange member is interconnected to each of said first and second packing members at neck portions of said anterior portions of said first and second packing members.

10. The device of claim 9, wherein said flange member includes:
    a substantially planar surface; and
    first and second extensions, wherein said first extension of said flange member is molded to said first packing member, and wherein said second extension of said flange member is molded to said second packing member.

11. The device of claim 10, wherein said substantially planar surface has at least a first dimension, wherein said first dimension is at least four times the width of said anterior portion of one of said first and second packing members.

12. The device of Claim 11, wherein said first and second extensions protrude from said substantially planar surface.

13. The device of claim 11, wherein at least most of said length of said first and second packing members is at an angle to said substantially planar surface.

14. The device of claim 1, wherein said planar sidewalls begin at the section of the device including the integral extension of said flange member and said neck portion, and wherein in said expanded condition an angle between said pair of sidewalls of said absorbent packing member is between about 10 and about 45 degrees.

15. The device of claim 1, wherein said width of said posterior portion of said packing member is from about 2 mm to about 10 mm when said packing member has not absorbed a fluid, and wherein said width of said posterior portion of said packing member is from about 5 mm to about 30 mm after said packing member has absorbed a fluid.

16. The device of claim 15, wherein a width of said packing member at said anterior portion does not increase when said packing member has absorbed a fluid.

17. The device of claim 5, wherein said substantially planar portion of said flange member is at least about 10 mm across, and wherein said extension of said flange member extends for at least 3 mm from said substantially planar surface.

18. The device of claim 1, wherein said length of said packing member is from about 10 mm to about 100 mm.

19. The device of claim 1, wherein the width of the packing member does not decrease from the anterior portion to the end of the sidewalls proximate to the posterior portion.

20. A device for treating nosebleeds, comprising:
   means for absorbing blood, said means for absorbing blood including:
      means for preventing movement of said device outwardly with respect to a nasal cavity;
      a pair of sidewalls;
      an anterior portion;
      a posterior portion with a free end;
      a neck portion proximate to said anterior portion and between said anterior portion and said posterior portion; and wherein in an expanded state of said means for absorbing blood a distance between said sidewalls increases at each point along said sidewalls of said means for absorbing blood from said neck portion to a second end of said side walls at said posterior portion, wherein said sidewalls of said means for absorbing blood are symmetrical about a central axis of said means for absorbing blood, wherein said means for absorbing blood is formed from a unitary piece of absorbent foam, and wherein said unitary piece of absorbent foam is free from any cover;
   means for blocking a view of blood interconnected to said means for absorbing blood, said means for blocking a view of blood including:
      means for preventing movement of said device inwardly with respect to said nasal cavity, wherein said means for absorbing blood is fused to said means for blocking a view of blood at said neck portion such that said neck portion is non-absorbent.

21. The device of claim 20, wherein said means for absorbing blood has a length defining a longitudinal axis, wherein said means for blocking a view of blood has at least a first surface defining a plane, and wherein said longitudinal axis is at an angle of other than 90 degrees to said plane.

22. The device of claim 20, further comprising first and second means for absorbing blood, wherein said first and second means for absorbing blood are molded to said means for blocking a view of blood.

23. The device of claim 20, wherein said means for preventing movement of said device outwardly with respect to a nasal cavity includes the width of the posterior portion increasing in a direction away from the anterior portion.

24. The device of claim 20, wherein said means for preventing movement of said device outwardly with respect to a nasal cavity includes the width of the means for absorbing blood increasing from the anterior portion to the posterior portion.

25. A method for treating nosebleeds, comprising:
   inserting a packing member into an existing nasal cavity, wherein the packing member is formed from an absorbent material, wherein the packing member is connected to a flange member at a non-absorbent neck near an anterior portion, wherein the packing member has a length with an anterior portion and a posterior portion, wherein the posterior portion is near a free end of the packing member, and wherein the packing member has a pair of sidewalls that extend along most of a length of the packing member;
   stopping insertion when said flange member contacts an area of the nose proximate to the existing nasal cavity; and
   absorbing fluid with the packing member, wherein the packing member expands along the length of the sidewalls against at least first and second walls of the existing nasal cavity, wherein after absorbing fluid and unconstrained by the cavity walls the packing member increases in width from a first end of the sidewalls at the non-absorbent neck in a direction away from the anterior portion, to a second end of the sidewalls at the posterior portion and wherein the posterior portion includes a widest portion of the packing member such that the sidewalls of the packing member are at an angle to one another of from 10 to 45 degrees.

26. The method of claim 25, further comprising: simultaneously inserting first and second packing members in first and second existing nasal cavities, wherein said first and second packing members are molded to a common flange member.

27. The method of claim 25, further comprising:
   positioning said flange member to substantially cover an opening to said existing nasal cavity, wherein a view of said nasal cavity is obscured.

28. The method of claim 25, wherein after said packing member absorbs fluid, said packing member increases in width from said anterior portion to said posterior portion.

29. The method of claim 25, wherein said flange member is fused to said packing member such that a non-absorbent neck portion is formed on the anterior portion of said packing member.

30. A method for absorbing fluids, comprising:
   providing a device including:
      a packing member formed from an absorbent foam with a pair of planar sidewalls having equal areas, an anterior portion and a posterior portion with a free end, wherein the packing member is not enclosed in a cover; and
      a flange member connected to the packing member near the anterior portion at a flange extension;

compressing the packing member so that the width of the packing member is of a first configuration in which the pair of planar sidewalls are substantially parallel to one another; and absorbing a fluid with the compressed packing member, wherein the packing member assumes an expanded state, wherein the width of the packing member is of a second configuration, wherein in the second configuration a distance between the planar sidewalls defining the width of the packing member increases such that the planar sidewalls are at an angle of between 10 and 15 degrees from an end of the sidewalls adjacent the flange extension to an opposite end of the sidewalls at least while expansion of the packing member is unconstrained such that the width along a majority of the length of the packing member generally increases from the anterior portion through at least some of the posterior portion, and wherein fluid is not absorbed at a neck portion abutting the end of the sidewalls adjacent the flange extension.

31. The method of claim 30, wherein said flange member is fused to said packing member such that a non-absorbent neck portion is formed on the anterior portion of said packing member.

* * * * *